United States Patent
Wang et al.

(10) Patent No.: US 7,518,359 B2
(45) Date of Patent: Apr. 14, 2009

(54) INSPECTION OF NON-PLANAR PARTS USING MULTIFREQUENCY EDDY CURRENT WITH PHASE ANALYSIS

(75) Inventors: Changting Wang, Niskayuna, NY (US); Ui Suh, Cincinnati, OH (US)

(73) Assignee: General Electric Company, Schenectady, NY (US)

(*) Notice: Subject to any disclaimer, the term of this patent is extended or adjusted under 35 U.S.C. 154(b) by 211 days.

(21) Appl. No.: 11/331,394

(22) Filed: Jan. 12, 2006

(65) Prior Publication Data

US 2006/0202687 A1  Sep. 14, 2006

Related U.S. Application Data

(63) Continuation-in-part of application No. 11/210,119, filed on Aug. 22, 2005, now Pat. No. 7,206,706.

(51) Int. Cl.
G01N 27/82  (2006.01)
(52) U.S. Cl. ............ 324/238; 324/237; 324/240; 702/38
(58) Field of Classification Search ............ 324/234, 324/238, 240, 237; 702/38
See application file for complete search history.

(56) References Cited

U.S. PATENT DOCUMENTS

| | | | |
|---|---|---|---|
| 3,971,982 A | 7/1976 | Tornblom | |
| 4,203,069 A | 5/1980 | Davis | |
| 4,271,393 A | 6/1981 | Hansen et al. | |
| 4,495,466 A | 1/1985 | Lakin | |
| 4,594,549 A | 6/1986 | Smith et al. | |
| 4,761,610 A | 8/1988 | Svegander et al. | |
| 5,311,128 A | 5/1994 | Lareau et al. | |
| 5,315,234 A | 5/1994 | Sutton, Jr. et al. | |
| 5,345,514 A | 9/1994 | Mahdavieh et al. | |
| 5,442,286 A * | 8/1995 | Sutton et al. ............ | 324/242 |
| 5,510,709 A | 4/1996 | Hurley et al. | |
| 5,610,517 A * | 3/1997 | Ma et al. ............ | 324/233 |
| 5,864,229 A | 1/1999 | Lund | |
| 5,969,260 A | 10/1999 | Belk et al. | |
| 6,420,867 B1 | 7/2002 | Goldfine et al. | |
| 6,657,429 B1 | 12/2003 | Goldfine et al. | |
| 6,784,662 B2 | 8/2004 | Schlicker et al. | |

(Continued)

FOREIGN PATENT DOCUMENTS

EP  1701157 A1  9/2006

(Continued)

OTHER PUBLICATIONS

European Search Report mailed May 22, 2007.

*Primary Examiner*—Patrick J Assouad
*Assistant Examiner*—David M. Schindler
(74) *Attorney, Agent, or Firm*—McNees Wallace & Nurick, LLC

(57) ABSTRACT

A non-planar part has a non-planar surface such as an edge, and may contain an anomaly such as a crack. The non-planar part is inspected using an eddy current technique. The method includes providing the non-planar part having the non-planar surface thereon, driving an eddy current probe at two or more frequencies, measuring an eddy current response signal of the non-planar part at each frequency, and performing a multifrequency phase analysis on the eddy current response signals.

12 Claims, 3 Drawing Sheets

U.S. PATENT DOCUMENTS

2003/0071615 A1    4/2003  Schlicker et al.
2003/0164700 A1    9/2003  Goldfine et al.
2004/0066188 A1*   4/2004  Goldfine et al. ............. 324/228
2005/0007108 A1    1/2005  Dogaru

FOREIGN PATENT DOCUMENTS

| JP | 57093250 A | 6/1982 |
| JP | 59009552 A | 1/1984 |
| JP | 59108955 A | 6/1984 |

* cited by examiner

INSPECTION OF NON-PLANAR PARTS USING MULTIFREQUENCY EDDY CURRENT WITH PHASE ANALYSIS

This application is a continuation-in-part of parent application Ser. No. 11/210,119, filed Aug. 22, 2005, now U.S. Pat. No. 7,206,706 for which priority is claimed and whose disclosure is incorporated herein by reference, and through the parent application further claims the benefit of U.S. Provisional Application No. 60/660,032, filed Mar. 9, 2005, the disclosure of which is hereby incorporated herein by reference.

This invention relates to the inspection of a part by the eddy current technique and, more particularly, to the multifrequency eddy current inspection of a non-planar part with phase analysis of the multifrequency eddy current signal.

BACKGROUND OF THE INVENTION

A number of non-destructive inspection techniques are in widespread use. These non-destructive inspection techniques allow a part to be inspected for anomalies without sectioning or etching the part, and without otherwise altering the structure of the part, which procedures in themselves add further anomalies to the part. Examples of non-destructive inspection techniques include ultrasonic testing, surface acoustic techniques, and eddy current inspection techniques. These techniques may be used to inspect new-make parts and parts that have previously been in service.

In the eddy current technique, a high-frequency alternating magnetic field applied at the surface of the part produces a responsive pattern of high-frequency electrical eddy currents within the part. The electrical eddy currents produce their own induced magnetic fields, which can be detected externally. The electrical eddy currents and their associated induced magnetic fields are normally regular in pattern, but the regularity is disrupted by the presence of anomalies in the part. Examples of anomalies include cracks, incipient cracks, inclusions at or near the surface, particles at or near the surface, and the like. By externally detecting the pattern of induced magnetic fields and their irregularities, the presence, size, and other features of the anomalies are deduced.

Eddy current inspection techniques have the important advantage that they allow the near-surface region of the part to be inspected nondestructively. Inspection of the near-surface region is important, because some mechanisms that produce premature failure of the part initiate at the surfaces of the part. In particular, anomalies such as cracks often initiate from surface edges or other non-planar regions of the part, where there are structural irregularities and/or stress concentrations. After surface-edge crack initiation, the cracks propagate into and through the remainder of the part, possibly resulting in a premature failure. Examples of such non-planar surface-edge crack-initiation sites include machined or cast edges between a front and a side of the part, intentionally produced holes such as fastener holes or large bores, intentionally produced cutouts such as the dovetail slots on the periphery of a turbine disk, and openings such as cooling holes.

The eddy current technique is used to detect the presence of the anomalies in as-manufactured (new-make) parts, and also in those parts after they have been in service, by periodic inspections. If no relevant indications of anomalies of a critical size are detected, the part may be placed into, or continued in, service. If anomalies of a critical size or larger are detected, the part is not continued in service, and is either repaired or scrapped.

One of the limitations on the use of the eddy current technique is the ability to discern an anomaly in the midst of background noise, a characteristic often expressed as the signal-to-noise ratio. For an anomaly to be reliably detected by the eddy current technique, the signal-to-noise ratio of the anomaly must be sufficiently high that the anomaly is not confused with the background noise. Too low a signal-to-noise ratio of a particular kind of anomaly means that the anomaly cannot be reliably detected.

Non-planar surfaces of the part are significant sources of noise in the analysis of eddy current output signals. Because these non-planar surfaces are the common locations where cracks or other anomalies may often be found, the noise associated with the non-planar surfaces of the part may mask the embryonic anomalies. The value of the eddy current technique is thereby lessened.

There is a great need for a technique by which eddy current detection of non-planar disturbances in the non-planar regions of parts may be accomplished with an increased signal-to-noise ratio as compared with current approaches, achieving more reliable detection of the anomalies. The present invention fulfills this need, and further provides related advantages.

SUMMARY OF THE INVENTION

The present invention provides a technique which is based on eddy current testing, but which achieves an improved signal-to-noise ratio of anomalies located in and near the non-planar region of the surface of the non-planar part being inspected. The advantages of conventional eddy current testing are retained, but the detectability of anomalies such as cracks at or near the non-planar regions of the surface of the part is improved. The present approach may be used with all such non-planar parts.

In accordance with the invention, a method for inspecting a non-planar part using an eddy current technique comprises the steps of providing the non-planar part, driving an eddy current probe at two or more frequencies, measuring an eddy current response signal of the non-planar part at each frequency, and performing a multifrequency phase analysis on the eddy current response signals.

The non-planar surface of the non-planar part has a non-planar feature (e.g., an edge) thereon. The non-planar part typically may have an anomaly (e.g., a crack) therein. In a typical situation, the anomaly is at or near the non-planar feature of the non-planar surface. That is, the eddy current response signal of the anomaly has its signal-to-noise ratio reduced by an eddy current response signal (i.e., noise) of the non-planar surface.

In one example of an application of interest, the present approach is utilized to detect a crack that is at or close to an edge of the non-planar surface. Noise in the eddy current response signal arising from the presence of the edge can otherwise interfere with the detection of the crack by masking or partially masking the presence of the crack in the background noise. The present approach improves the ability to identify and map the location of the crack by increasing the signal-to-noise ratio of the eddy current response signal produced by the crack. The eddy current probe is scanned over the non-planar part to produce an eddy current mapping of the non-planar part and any cracks therein. The present approach increases the signal-to-noise ratio of the cracks that are at or near the edge so that they may be more accurately evaluated.

The eddy current probe may be driven at any grouping of two or more frequencies that are otherwise operable with eddy current technology. Those skilled in the art are familiar with the frequencies operable in any selected eddy current application, which are selected according to the size and type of the anomaly being sought, the geometry of the non-planar part, the material from which the non-planar part is made, and other considerations.

The step of performing preferably includes the steps of mixing the eddy current response signals of the two or more frequencies to form a mixed signal, level shifting a real component of the mixed signal to confine the phase of the mixed signal to the range between −180 and +180 degrees, and obtaining phase and magnitude images of the non-planar part.

In accordance with a further embodiment, an inspection system operable to inspect a non-planar part for a possible anomaly therein comprises an eddy current probe configured to induce eddy currents in the non-planar part, and an eddy current instrument coupled to the eddy current probe. The eddy current instrument is configured to apply a plurality of multifrequency excitation signals to the eddy current probe to generate a plurality of multifrequency response signals from the non-planar part. A processor is configured to analyze the multifrequency response signals from the eddy current instrument by performing a multifrequency phase analysis, to inspect the non-planar part for the presence of the crack.

The present approach produces a signal with an increased signal-to-noise ratio in eddy current testing of an anomaly at or near the non-planar portion of a non-planar part. The increased signal-to-noise ratio allows the anomaly to be more readily detected and visualized. A common initiation site for premature failure related to the anomaly is at or near the non-planar region of the non-planar part, and the present approach therefore provides an important practical advance over prior techniques.

Other features and advantages of the present invention will be apparent from the following more detailed description of the preferred embodiment, taken in conjunction with the accompanying drawings, which illustrate, by way of example, the principles of the invention. The scope of the invention is not, however, limited to this preferred embodiment.

DETAILED DESCRIPTION OF THE INVENTION

Figure 1:
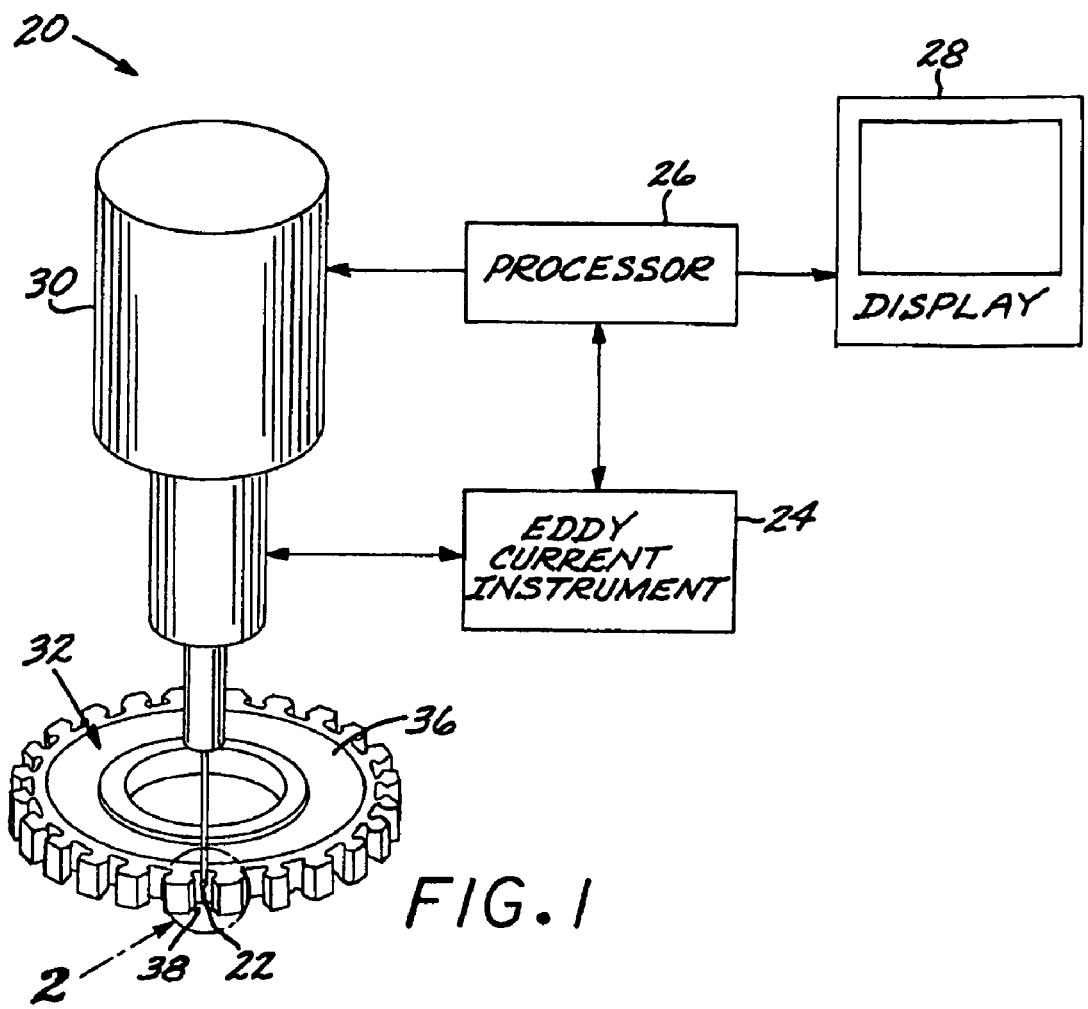
FIG. 1 schematically depicts an eddy current inspection system for a non-planar part with an edge.

FIG. 1 depicts an exemplary inspection system 20 for performing the inspection of non-planar parts. As used herein, a "part" includes any object being inspected by the present approach, including but not limited to articles, components, structures, test specimens, and the like. A "non-planar part" is such an object wherein the surface of the region of the part being inspected is not planar. That is, it has an edge, a contour, or other non-planar surface feature.

The inspection system 20 includes an eddy current probe 22, an eddy current instrument 24, a processor 26, and a display 28, all interconnected by appropriate cabling. The physical configuration of such inspection systems 20 is known in the art, except for the improvements discussed herein. The eddy current probe 22 is configured to induce eddy currents in a non-planar part 32 and to measure the resulting eddy current response signals, in order to inspect the non-planar part 32. Such eddy current probes are known in the art.

The eddy current probe 22 may be stationary or, preferably, may be moved relative to the non-planar part 32. The movement of the eddy current probe 22 relative to the non-planar part 32 may be accomplished manually or in an automated fashion. The eddy current probe 22 is optionally but preferably mounted on a scanner 30 that positions and moves the eddy current probe relative to a stationary non-planar part 32. (Equivalently, the non-planar part 32 may be moved and the eddy current probe 22 held stationary.) The optional scanner 30 may be of any type, but is typically a multi-axis numerically controlled device controlled by the processor 26. The scanner 30 provides translation and rotation of the eddy current probe 22 as may be required for the specific type of non-planar part 32. The scanner 30 precisely positions the eddy current probe 22 relative to the non-planar part 32 and moves the eddy current probe 22 in a stepped, rastered fashion.

Figure 2:
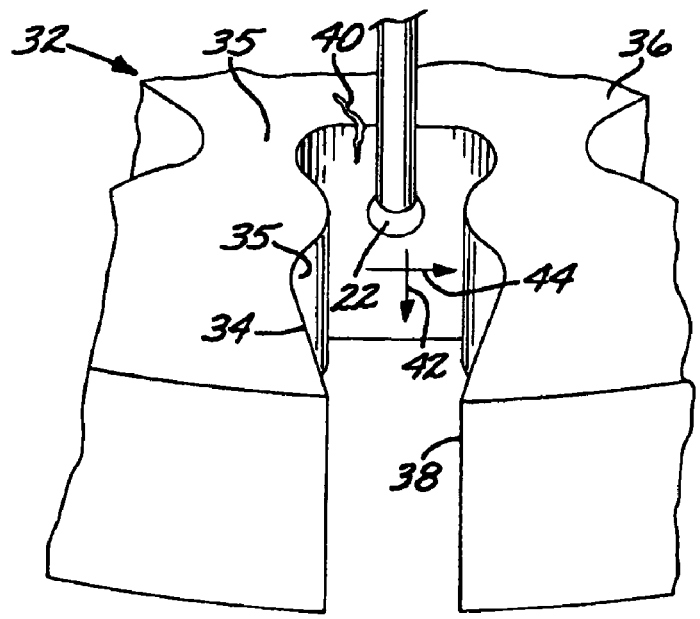
FIG. 2 is a schematic detail, taken in region 2 of FIG. 1, showing the dovetail engagement being inspected.

As shown in FIG. 2, the non-planar part 32 has a non-planar edge 34 thereon as an example of a non-planar surface 35, and the inspection is conducted at or near the edge 34. As used herein, "at or near" means that an eddy current response signal (i.e., the signal of interest) of any anomaly in the non-planar part 32 has its signal-to-noise ratio reduced by an eddy current response signal (i.e., noise) of the non-planar surface 35 of the non-planar part 32, in this case the non-planar edge 34. An "anomaly" is a feature of interest that is detectable above the background noise by the eddy current technique and whose signal-to-noise ratio may be improved by the present approach. Examples of anomalies include cracks, incipient cracks, inclusions at or near the surface, particles at or near the surface, and the like. The presence of the non-planar edge 34 produces noise in the eddy current response signals, and the present approach improves the signal-to-noise ratio of the eddy current response signals. There are a large number of types of non-planar parts 32 that may have contours or edges 34 thereon. In the illustrations of FIGS. 1 and 2, the non-planar part 32 is a turbine disk 36, and the inspected non-planar surface 35 is a portion of a disk slot 38 on the outer periphery of the turbine disk 36 that has an edge 34. Other types of non-planar surfaces include, for example, machined or cast edges between a front and a side of the non-planar part, a leading edge of an airfoil (such as a turbine blade or vane), a trailing edge of the airfoil, a blade root of the airfoil, intentionally produced holes such as fastener holes or large bores, and openings such as cooling holes. In the present approach, the eddy current probe 22 may have any configuration operable for the type of non-planar part 32 being inspected. The physical configuration and electrical characteristics of the eddy current probe 22 are typically optimized for each type of non-planar part 32.

The edge 34 has an associated stress concentration when loaded in service. Consequently, anomalies such as a crack 40 illustrated in FIG. 2 may preferentially initiate at or near the edge 34, and then propagate through the non-planar part 32 to cause premature failure. The crack 40 is illustrated as a surface edge crack, but it may be a surface near-edge crack, or a subsurface edge or near-edge crack as well. The eddy current inspection system 20 is used to detect such a crack 40 at an early stage, before it can propagate to produce premature failure. Once detected after reaching a sufficiently large size, the crack 40 may be repaired using known techniques, or, if the crack 40 cannot be repaired, the non-planar part 32 is removed from service. The noise that is otherwise present in the eddy current response signal associated with the edge 34 tends to mask the presence of the crack 40.

Figure 3:
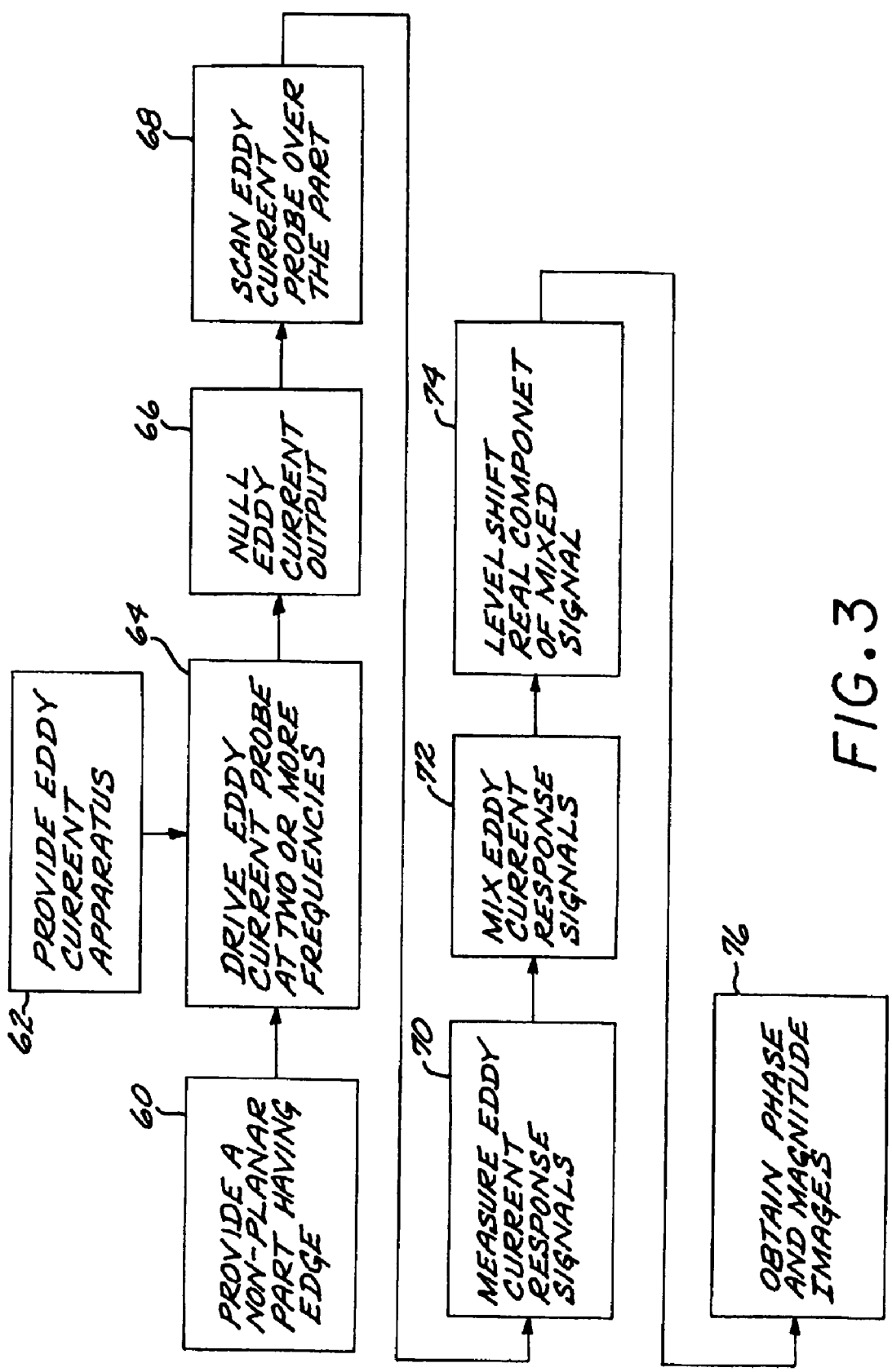
FIG. 3 is a block flow diagram of an embodiment of a method for practicing the present invention.

FIG. 3 depicts the steps in an embodiment of the present approach. The non-planar part 32 having the edge 34 is provided, step 60. The eddy current apparatus, including the eddy current probe 22, the eddy current instrument 24, the processor 26, and preferably the display 28, is provided, step 62. The eddy current probe 22 is positioned adjacent to the non-planar part 32, as illustrated in FIGS. 1 and 2. In general, when the eddy current probe 22 is driven with an alternating-frequency voltage, alternating magnetic fields are produced in the coil(s) of the eddy current probe 22. Eddy currents are responsively produced in the non-planar part 32. These eddy currents are regular in form, except when they are disturbed by the presence of the crack 40 (an example of an anomaly). The eddy current produces a secondary field, which is measured by the eddy current probe coil or by other types of sensors in the eddy current probe as an eddy current response signal. The measured eddy current response signal is converted to an electrical output, which in turn is provided to the eddy current instrument 24 and thence to the processor 26 for analysis.

In the present approach, the eddy current probe 22 is driven at two or more frequencies, step 64. For the illustration, two frequencies, $f_1$ and $f_2$, are used, but additional frequencies $f_3 \ldots f_n$ may be utilized as well. The eddy current probe 22 is preferably driven simultaneously with all of the frequencies, but it may be driven sequentially with these frequencies. The selected frequencies may be any two or more frequencies that are operable in an eddy current inspection system. No specific frequencies may be identified, because the selection of the frequencies to be used is responsive to considerations such as the size and type of the anomaly being sought, the geometry of the non-planar part, the material from which the non-planar part is made, and other considerations.

The processor 26 is configured to analyze the output of the eddy current instrument 24, and thence the eddy current probe 22, as will be described next.

The eddy current output is first nulled, step 66. That is, the eddy current output is set to a reference zeroed value as the baseline for the further analysis.

The eddy current probe 22 is scanned in a series of steps over the non-planar surface 35 of the non-planar part 32, step 68. In the example illustrated in FIG. 2, the eddy current probe 22 is incrementally scanned in a vertical direction 42 in a series of discrete steps, and thereafter indexed in a horizontal direction 44. The discrete steps in the vertical direction 42 are then repeated at the new index location. This process is repeated until a sufficiently large sampling of the non-planar surface 35 of the non-planar part 32 is achieved. This scanning process is achieved by the scanner 30 under programmed control of the processor 26.

At each of the stepped locations, the eddy current response signals produced by the eddy current instrument 24 are measured, step 70, at each of the frequencies, in this example frequencies $f_1$ and $f_2$. The results may be displayed as separate images of the non-planar part, image $I_1$ at frequency $f_1$ and image $I_2$ at frequency $f_2$. Any crack 40 that is present may or may not be seen in these images. If the crack 40 is seen imperfectly or not at all, the likely cause is that the noise produced in the images $I_1$ and $I_2$ by the edge 34 obscures the image that is produced by the presence of the crack 40. Typically, the image at one frequency is better than the others, but the images have a significant noise component in their real and imaginary parts due at least in part to the edge-induced noise.

The present approach takes the analysis further by processing the eddy current response signals in the processor 26 by a phase-analysis approach. The phase-analysis approach is based on the different magnitude and phase eddy current responses for different driving frequencies $f_1$ and $f_2$ (and other frequencies where used). The additional information provided by the multifrequency eddy current response signals along with phase information is used to reduce the undesired noise created at non-planar surfaces such as edges, enhance the desired signal-to-noise ratio, and provide additional information to reduce false indications of the anomalies such as the crack 40.

The number of frequencies needed for the generation of the multifrequency response signals may be selected based upon the number of undesired noise features to be eliminated or reduced. In a particular non-planar-part embodiment of the present invention, the selected number of frequencies is greater than the number of undesired noise features to eliminate with an assumption that an anomaly in the non-planar part under test and any non-relevant indications to be suppressed do not cause the same phase and magnitude change in the eddy current signal at different frequencies or, alternatively, the eddy current probe response in X-Y plots at different frequencies are not collinear after a phase angle rotation. The generated multifrequency eddy current response signals are included in a multifrequency response data set. As used herein, a "multifrequency response data set" refers to a data set that comprises the entire set of response signals that are generated as a result of the eddy currents induced in the inspected non-planar part under consideration by application of the multifrequency excitation signals to the eddy current probe.

According to the present approach, the reference data set refers to a data set that is relatively free from anomalies but is dominated by undesired noise features. The reference data set comprises at least two frequency response signals at different frequencies. The two frequency response signals may be represented as follows:

$$f_1: x_1(t) = X_d(t) \angle \theta_d(t) + X_n(t) \angle \theta_n(t) \tag{1}$$

$$f_2: x_2(t) = k_d(t) X_d(t) \angle (\theta_d(t) + \Delta\theta_d(t)) + k_n(t) X_n(t) \angle (\theta_n(t) + \Delta\theta_n(t)) \tag{2}$$

The quantities $f_1$ and $f_2$ represent two exemplary eddy current frequencies for a two-frequency eddy current inspection, $x_1(t)$ and $x_2(t)$ represent the eddy current response signals corresponding to the frequencies $f_1$ and $f_2$ at position (or time) t, $X_d(t)$ represents the magnitude of undesired noise features in the response signal, $k_d(t)$ represents a coefficient reflecting a change in the magnitude of the response signal, $k_n(t)$ represents a coefficient reflecting the change in the noise in the response signal, $\angle(\theta_d(t)$ represents the phase angle of the crack in the response signal, $\angle\theta_n(t)$ represents the phase angle of undesired noise features in the response signal, $\Delta\theta_d(t)$ represents the phase change of the crack in the response signal, and $\Delta\theta_n(t)$ represents the phase change of the undesired noise feature in the response signal. Preferably, the two frequencies $f_1$ and $f_2$ are selected such that $(\Delta\theta_d(t) - \Delta\theta_n(t))$ is in a range of from about 135° to about 225°. Most preferably, the two frequencies $f_1$ and $f_2$ are selected such that $(\Delta\theta_d(t) - \Delta\theta_n(t))$ is about 180°.

The eddy current response signals are mixed, step 72, to determine a set of processing parameters. The processing parameters may correspond to the coefficients $k_d(t)$ and $k_n(t)$. Each of the frequency response signals $x_1(t)$ and $x_2(t)$ have a real component and an imaginary component. In one form, the mixing 72 is accomplished by initially rotating the phase of one of the frequency response signals and scaling the real component and the imaginary component of one of the frequency response signals. As shown in equation (3), the response vector $x_2(t)$ is rotated by $\Delta\theta_n(t)$ to yield $x_2'(t)$:

$$f_2: x_2'(t) = k_d(t)X_d(t)\angle(\theta_d(t)+\Delta\theta_d(t)-\Delta\theta_n(t))+k_n(t)X_n(t) \angle(\theta_n(t)) \quad (3)$$

When $\theta_d(t) = \Delta\theta_n(t) = \theta(t)$ and $k_d(t) = k_n(t) = k(t)$, $x_2(t)$ becomes $k(t)x_1(t)$ with a phase rotation. This condition represents the "collinearity" condition, specifically that the eddy current response in X-Y plots at different frequencies is collinear after a phase angle rotation. In some embodiments, a time shift operation may also be performed on at least one of the frequency response signals.

A mixed frequency response signal is then obtained as shown in equation (4) by subtracting the first frequency response signal from a rotated and scaled second frequency response signal. The rotated second frequency response signal $x_2'(t)$ is scaled by the coefficient $1/k_n(t)$ on both sides and reduced by the frequency response signal $x_1(t)$ to obtain a mixed signal $x_{12}(t)$.

Mixing $f_1$ and $f_2$: \quad (4)

$$\begin{aligned} x_{12}(t) &= x_2'(t)/k_n(t) - x_1(t) \\ &= (k_d(t)/k_n(t))X_d(t)L(\theta_d(t) + \\ &\quad \Delta\theta_d(t) - \Delta\theta_n(t)) - X_d(t)L(\theta_d(t)) \end{aligned}$$

With the rotation and scaling operation, the noise factor in equation (4) is eliminated after the multifrequency mixing operation. A noise-filtered response signal is generated based upon the processing parameters. This process minimizes a residual, which represents undesired noise features in the two frequency response signals, after the mixing operation.

The processing parameters obtained from step 72 are applied to the entire multifrequency response signal data set generated by equation (4) to generate a noise-filtered data set. The resultant noise-filtered data set includes both real and imaginary components with improved signal-to-noise ratio.

The real components of the mixed signal $x_{12}(t)$ are level shifted as necessary above or below zero so that the phase is within the dynamic range, step 74.

The preceding analysis is performed at each spatial point in the stepped pattern of responses in order to obtain phase images, corresponding to the magnitude images discussed previously, step 76. Further in this step, a phase analysis is performed on the noise-filtered data set, where an offset is applied to the horizontal component to suppress noise sensitivity. The data from the phase analysis contains information correlated with the anomaly, and provides additional discrimination to reduce false positive indications. When the phase changes are different, $\Delta\theta_d(t) \neq \Delta\theta_n(t)$, and the magnitude changes are different, $k_d(t) \neq k_n(t)$, the mixed signal $x_{12}(t)$ represents a crack signal with the undesired edge noise eliminated. In one embodiment, the phase $\theta(t)$ and its rotation $\Delta\theta(t)$ with frequency are functions of the probe position while scanning over the crack. As a result, the residual between the noise terms in equations (1) and (2) are substantially reduced but are not necessarily zero at different positions or time (t) after multi-frequency mixing, and therefore the mixed signal retains desired flaw signals and provides an improved signal-to-noise ratio.

Figure 4:
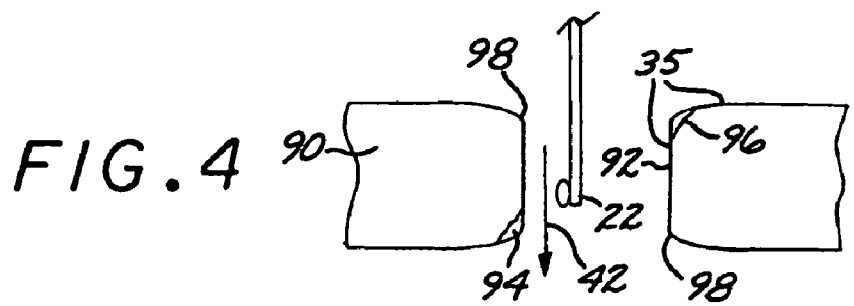
FIG. 4 is a schematic illustration of a physical configuration of a first reduction to practice of the present approach.
Figure 5:
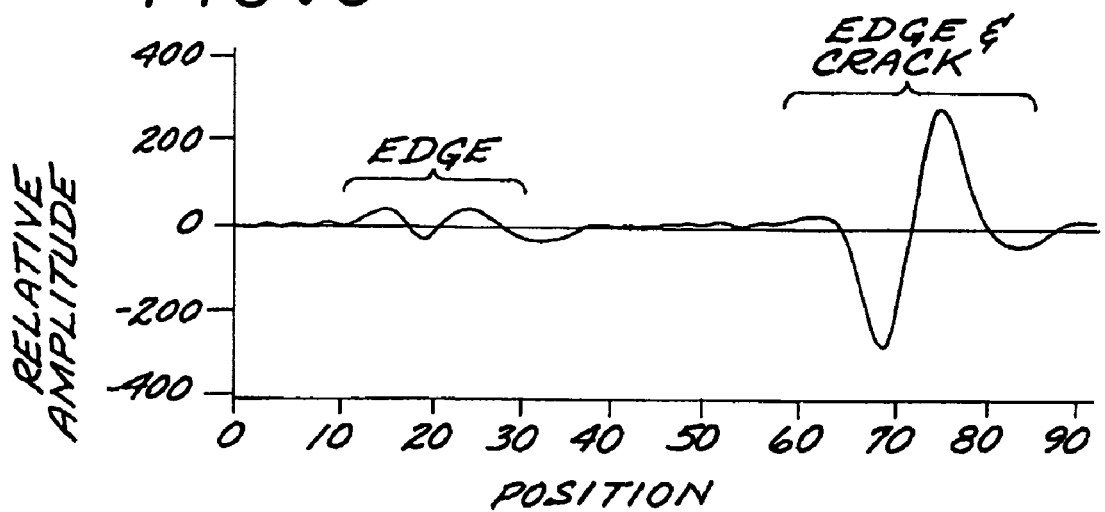
FIG. 5 is a graph of relative amplitude as a function of position for an unprocessed eddy current response measured from the configuration of FIG. 4.
Figure 6:
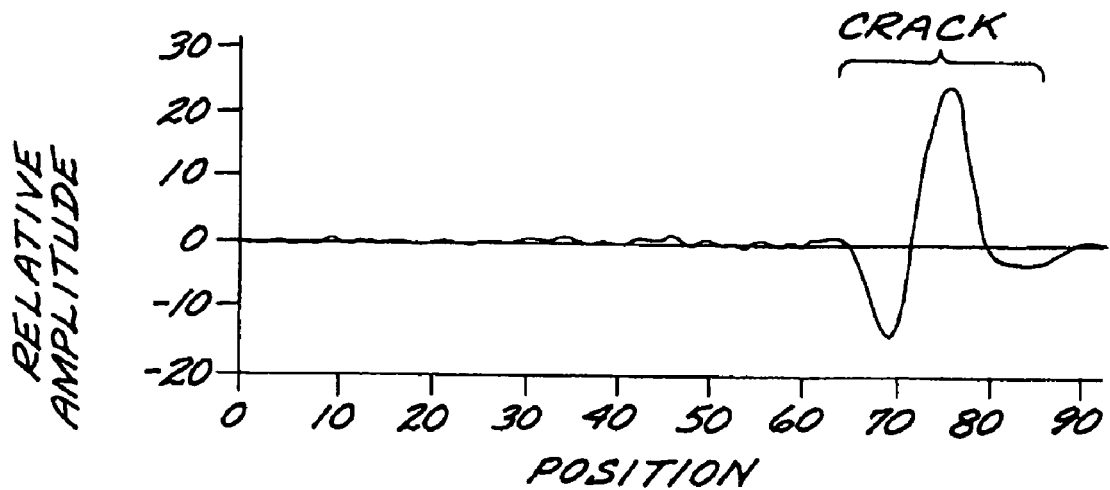
FIG. 6 is a graph of relative amplitude as a function of position for eddy current response data measured from the configuration of FIG. 4, and processed according to the present multifrequency eddy current phase analysis approach.

The present approach has been reduced to practice with excellent results. FIG. 4 depicts the configuration of a first reduction to practice wherein a part 90 has a bolt hole 92 therein, thereby defining the non-planar surface 35. Two cracks 94 and 96 were intentionally introduced into the top surface and the bottom surface of the non-planar part 90 at the periphery of the bolt hole 92. The intersection of the top and bottom surfaces with the bolt hole 92 define edges 98. The non-planar part 90 with the bolt hole 92 and the cracks 94 and 96 was through-thickness scanned with the multifrequency eddy current probe 22 in the vertical (scan) direction 42. FIGS. 5 and 6 are graphs of amplitude as a function of position of the unprocessed (i.e., raw) eddy current response signal (FIG. 5) for the edge and the edge+crack, and the result of applying the multifrequency phase analysis to the signal of FIG. 5 (FIG. 6). The edge noise signal produced by the edges 98 is virtually eliminated in the multifrequency-phase-analysis results of FIG. 6. In this example, the crack 96 was made large and pronounced, so that its eddy current response signal was not completely masked by the noise, but in other situations the edge noise may partially or fully mask the eddy current response signal of the crack.

In a second reduction to practice, two cracks were intentionally introduced in a specimen at a location along a long, straight edge. The two cracks were eddy-current scanned using the approach described earlier. The unprocessed data had a maximum signal-to-noise ratio for the first crack of 1.9 at $f_1$ and 1.6 at $f_2$. The multifrequency phase analysis of the first crack resulted in a maximum signal-to-noise ratio of 15.9. The unprocessed data had a maximum signal-to-noise ratio for the second crack of 2.7 at $f_1$ and 2.4 at $f_2$. The multifrequency phase analysis of the second crack resulted in a maximum signal-to-noise ratio of 17.8. The improvements in the signal-to-noise ratio for the first crack and the second crack were, respectively, factors of 8.3 and 6.6.

The present approach thus provides a method for performing eddy current inspection of an anomaly, such as a crack, in a non-planar part with a significantly improved signal-to-noise (i.e., contrast) ratio as compared with the unprocessed eddy current response.

Although a non-planar particular embodiment of the invention has been described in detail for purposes of illustration, various modifications and enhancements may be made without departing from the spirit and scope of the invention. Accordingly, the invention is not to be limited except as by the appended claims.

What is claimed is:

1. A method for inspecting a non-planar part using an eddy current technique, comprising the steps of
    providing the non-planar part;
    driving an eddy current probe at two or more frequencies;
    measuring an eddy current response signal of the non-planar part at each frequency; and
    performing a multifrequency phase analysis on the eddy current response signals, wherein performing the multifrequency phase analysis includes the steps of
    mixing the eddy current response signals of the two or more frequencies to form a mixed signal,
    level shifting a real component of the mixed signal to confine the phase of the mixed signal to the range between −180 and +180 degrees, and
    obtaining phase and magnitude images of the non-planar part.

2. The method of claim 1, wherein the step of providing includes the step of
  providing the non-planar part having an anomaly therein.
3. The method of claim 1, wherein the step of providing includes the step of
  providing the non-planar part having a crack therein.
4. The method of claim 1, wherein the step of providing includes the steps of
  providing the non-planar part having an anomaly therein, and
  providing the non-planar part having a non-planar surface thereon, and wherein the anomaly is at or near the non-planar surface.
5. The method of claim 1, wherein the step of providing includes the step of
  providing the non-planar part having a crack therein intersecting an edge.
6. The method of claim 1, including an additional step of scanning the eddy current probe over the non-planar part.
7. A method for inspecting a non-planar part using an eddy current technique, comprising the steps of
  providing the non-planar part having an edge thereon;
  driving an eddy current probe at two or more frequencies;
  scanning the eddy current probe over the non-planar part;
  measuring an eddy current response signal of the non-planar part at each frequency; and
  performing a multifrequency phase analysis on the eddy current response signals, wherein the step of performing includes the steps of
    mixing the eddy current response signals of the two or more frequencies to form a mixed signal,
    level shifting a real component of the mixed signal to confine the phase of the mixed signal to the range between −180 and +180 degrees, and
    obtaining phase and magnitude images of the non-planar part.
8. The method of claim 7, wherein the step of providing includes the step of
  providing the non-planar part having an anomaly therein.
9. The method of claim 7, wherein the step of providing includes the step of
  providing the non-planar part having a crack therein.
10. The method of claim 7, wherein the step of providing includes the steps of
  providing the non-planar part having an anomaly therein, and
  providing the non-planar part having a non-planar surface thereon, and wherein the anomaly is at or near the non-planar surface.
11. The method of claim 7, wherein the step of providing includes the step of
  providing the non-planar part having a crack therein intersecting the edge.
12. The method of claim 7, including an additional step of scanning the eddy current probe over the non-planar part.

* * * * *